United States Patent [19]

Findeisen

[11] 4,143,068
[45] Mar. 6, 1979

[54] PROCESS FOR THE PREPARATION OF ACYL CYANIDE COMPOUNDS

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 777,288

[22] Filed: Mar. 11, 1977

[30] Foreign Application Priority Data

Apr. 2, 1976 [DE] Fed. Rep. of Germany ....... 2614242

[51] Int. Cl.$^2$ ...................... C07C 51/54; C07C 120/00
[52] U.S. Cl. ............................. 260/545 R; 260/347.8; 260/332.3 R; 260/332.3 P; 260/326.5 A; 260/307 H; 260/307 R; 260/307 D; 260/308 R; 260/308 A; 260/308 B; 260/464; 260/465.5 R; 260/465 F; 260/465.1; 260/465 R; 260/465 G; 544/106; 548/373; 548/375; 548/377; 548/378; 548/335; 560/155; 560/19; 560/125
[58] Field of Search ......... 260/545 R, 347.8, 332.3 R, 260/332.3 P, 326.55, 307 H, 307 R, 307 D, 308 R, 308 A, 308 B, 464, 465 R, 465.1; 544/106; 548/337, 338, 339, 373, 375, 377, 378, 335; 560/155, 19, 125

[56] References Cited
PUBLICATIONS

Smith, "The Chemistry of Open–Chain Organic Nitrogen Compounds", vol. I, (1965), p. 218.

Thesing et al., Angew. Chem., vol. 68, pp. 425-435, (1956).

*Primary Examiner*—Gerald A. Schwartz
*Attorney, Agent, or Firm*—Sprung, Felfe, Horn, Lynch & Kramer

[57] ABSTRACT

Acyl cyanides of the formula

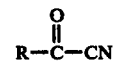

wherein
R is alkyl or substituted alkyl with 1 to 8 carbon atoms, or cyano-carbonyl substituted alkyl, i.e., containing another

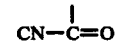

group, cycloalkyl or substituted cycloalkyl with 3 to 12 carbon atoms or aryl or substituted aryl or represents an optionally substituted 5-membered or 6-membered heterocyclic radical which can additionally also be fused with a benzene ring,
are made by reacting the corresponding acid halide with an alkali metal cyanide or anhydrous hydrocyanic acid in the presence of a heavy metal cyanide and optionally in the presence of a diluent, at a temperature of between 100° C. and 300° C.

24 Claims, No Drawings

PROCESS FOR THE PREPARATION OF ACYL CYANIDE COMPOUNDS

The present invention relates to a process for the preparation of certain acyl cyanide compounds. These compounds are useful as starting materials for the synthesis of herbicides.

It is known that acyl cyanides can be prepared by reacting acyl halides with metal cyanides (see Angew. Chem. 68, 425–448 (1956)). However, this process has a number of disadvantages. Thus, for example, it is expensive and can be carried out on a commercial scale only with difficulty since it is a two-phase reaction in which a solid is reacted with a liquid or with a substance present in solution. Moreover, the reaction does not give a single reaction product but a mixture of substances which is difficult to separate and which also contains, in addition to the particular acyl cyanide, a relatively large amount of a corresponding dimer. Accordingly, the yields of the acyl cyanide are relatively low. A further disadvantage of this process is that the washing water obtained during working up has to be subjected to thorough purification before it is run off since it still contains considerable amounts of highly toxic metal cyanides which are used in excess during the reaction.

Furthermore, it has been disclosed that aroyl cyanides can be synthesised by reacting arylcarboxylic acid chlorides with hydrocyanic acid, in the presence of pyridine as an acid-binding agent, in absolute ether (see Angew. Chem. 68, 425–488 (1956)). However, this process also is associated with several disadvantages. Thus, firstly, it is not generally applicable. Moreover, it is technically very involved because the operation with pyridine, which is highly toxic, and with ether, which is readily inflammable, demand particularly stringent safety precautions. Moreover, in this case also thorough purification of the washing water obtained during working up is unavoidable because of the pyridine dissolved therein. The fact that a considerable amount of dimeric aroyl cyanide is formed during the reaction is also a disadvantage since, as a result of this, both the yield of aroyl cyanide is generally reduced and the isolation there of is made more difficult.

The present invention now provides a process for the preparation of an acyl cyanide of the general formula

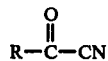 (I), in which
R is alkyl or substituted alkyl with 1 to 8 carbon atoms, or cyano-carbonyl substituted alkyl, i.e., containing another

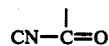

group, cycloalkyl or substituted cycloalkyl with 3 to 12 carbon atoms or aryl or substituted aryl or represents an optionally substituted 5-membered or 6-membered heterocyclic radical which can additionally also be fused with a benzene ring,
which process comprises reacting an acid halide of the general formula

 (II), in which
R is alkyl or substituted alkyl with 1 to 8 carbon atoms (and wherein R can contain another

group), cycloalkyl or substituted cycloalkyl with 3 to 12 carbon atoms or aryl or substituted aryl or represents an optionally substituted 5-membered or 6-membered heterocyclic radical which can additionally also be fused with a benzene ring, and
X represents halogen, preferably fluorine, chlorine or bromine,
with an alkali metal cyanide or anhydrous hydrocyanic acid in the presence of a heavy metal cyanide and optionally in the presence of a diluent, at a temperature of between 100° C. and 300° C.

Preferably, R represents straight-chain or branched alkyl with 1 to 4 carbon atoms, which can optionally carry one or more substituents selected from alkoxy with 1 to 4 carbon atoms, carbalkoxy with 1 to 4 carbon atoms in the alkoxy group, nitro, nitrile and halogen (namely fluorine, chlorine, bromine or iodine); cycloalkyl with 5 or 6 carbon atoms in the ring system, which optionally carries one or more substituents selected from alkyl with 1 to 4 carbon atoms, alkoxy or carbalkoxy with, in either case, up to 4 carbon atoms in the alkyl part, nitro, nitrile and halogen (for example fluorine, chlorine and bromine); phenyl or naphthyl, either of which can optionally carry one or more substituents selected from alkyl with 1 to 4 carbon atoms, alkoxy or carbalkoxy with, in each case, up to 4 carbon atoms in the alkyl part, nitro and halogen (for example fluorine, chlorine and bromine); or a 5-membered or 6-membered heterocyclic radical which can contain 1 to 3 heteroatoms, selected from oxygen, sulphur and nitrogen, in the ring and which optionally carries one or more substituent selected from alkyl with 1 to 4 carbon atoms, alkoxy or carbalkoxy with, in either case, up to 4 carbon atoms in the alkyl part, nitro, nitrile and halogen (for example fluorine, chlorine and bromine) and which optionally can be fused with a benzene ring.

Examples which may be mentioned of heterocyclic radicals which can be used are morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

It is to be regarded as extremely surprising that acyl cyanides of the formula (I) are accessible in high yield and excellent purity by the process according to the invention since, in view of the known state of the art, it was be expected that the same difficulties would arise with this process as in the case of the analogous reaction of acyl halides with alkali metal cyanides or heavy metal cyanides in a two-phase system.

In particular, it was in no way to be foreseen that the formation of undesired dimeric acyl cyanides can be completely suppressed when alkali metal cyanides or hydrocyanic acid are used in the presence of heavy metal cyanides.

The process according to the invention has a number of advantages. Thus, it is not restricted to the synthesis of a few specific compounds but has very broad application. Quite apart from this, it can also be carried out on an industrial scale in a relatively simple manner. With the process according to the invention, the acyl cyanides can be obtained in high yield and excellent purity, free from troublesome by-products. An additional decisive advantage of the process according to the invention is that working up present no problems.

The alkali metal halides which are formed in the course of the reaction are separated off from the acyl cyanide by filtration and the filtrate is subjected to a simple fractional distillation. The alkali metal halides formed are substances which are compatible with the environment and therefore do not signify a pollution of the environment.

If hydrocyanic acid in the presence of heavy metal cyanides is used for the conversion of acyl halides, the hydrogen halide acids formed can be isolated and used in other ways. The process according to the invention thus represents a valuable enrichment of the art.

If benzoyl chloride and anhydrous hydrocyanic acid are used as the starting materials and copper(I) cyanide is used as the catalyst, the course of the reaction can be represented by the following equation:

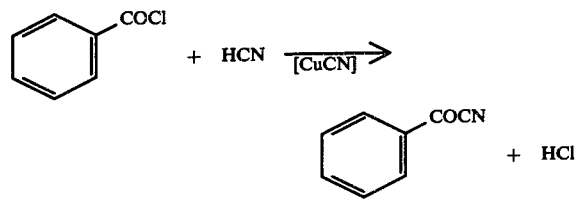

When benzoyl chloride and sodium cyanide are used in the presence of catalytic amounts of zinc(II) cyanide, the course of the reaction can be represented by the following equation:

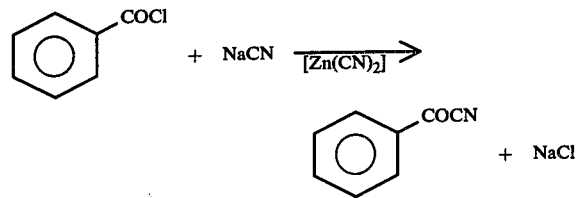

The acid halides of the formula (II) to be used as starting materials are known or can be prepared by methods which are known in principle. Preferred examples of acid halides of the formula (II) which may be mentioned are: acetyl chloride, acetyl bromide, propionyl chloride, propionyl bromide, cyclohexanecarboxylic acid chloride (or bromide), cyclopentanecarboxylic acid chloride (or bromide), benzoyl fluoride, benzoyl bromide, benzoyl chloride, m-chloro-benzoyl chloride, 3,5-dichloro-benzoyl chloride, naphthalene-1-carboxylic acid chloride, 1-phenyl-5-pyrazolone-3-carboxylic acid chloride, terephthalic acid dichloride, isophthalic acid dichloride and others. Aromatic acid halides, especially benzoyl halides, in particular benzoyl chloride, may be mentioned as being particularly preferred. The alkali metal cyanide is preferably sodium cyanide or potassium cyanide. Heavy metal cyanides, which are used in catalytic amounts, which may be mentioned are, in particular, cyanides of the metals of the first and second auxiliary group of the Periodic Table, such as copper(I) cyanide, copper(II) cyanide and zinc cyanide as well as their complex compounds with alkali metal cyanides, such as are formed, for example, when sodium cyanide is reacted with copper(I) cyanide:

$$3 \text{ NaCN} + \text{CuCN} \rightarrow \text{Na}_3\text{Cu(CN)}_4$$

Possible diluents which can be employed when carrying out the process according to the invention are all inert organic solvents which do not enter into a chemical reaction either with the acid chlorides or with the metal cyanides or hydrocyanic acid. In principle, it is also possible to carry out the reaction according to the invention without solvents.

The reaction temperature can be varied within a relatively wide range. In general, the reaction is carried out at temperatures of between 100° and 300° C. and preferably of between 150° and 250° C.

The process according to the invention is generally carried out under normal pressure. When low-boiling acid chlorides are converted, it is advisable to apply pressure in order to increase the conversion.

When carrying out the process according to the invention, in general stoichiometric amounts of the acid chloride are reacted with an alkali metal cyanide or anhydrous hydrocyanic acid in the presence of catalytic amounts of a heavy metal cyanide. However, the acid chloride can also be used in excess and in that case is advantageously even used as the solvent.

Working up is carried out after the reaction has ended, usually by distillation or recrystallisation. In a particular embodiment, the reaction according to the invention can also be utilised as a continuous reaction.

The mixture of the acid chloride and hydrocyanic acid can also be reacted, according to the invention, in the gas phase in the presence of catalytic amounts of a heavy metal cyanide.

The acyl cyanides of the formula (I) which can be prepared by the process according to the invention are valuable starting materials, for example for the synthesis of 1,2,4-triazin-5-ones, which possess outstanding herbicidal properties (see German Offenlegungsschrift (German Published Specification) No. 2,224,161).

Thus, for example, 3-methyl-4-amino-6-phenyl-1,2,4-triazin-5-one of the formula

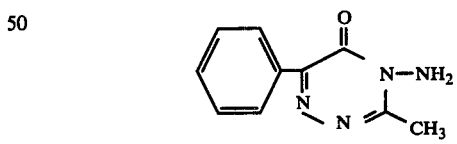

can be prepared by reacting benzoyl cyanide, in the presence of concentrated hydrochloric acid, with ethanol in a first stage and, in a second stage, reacting the resulting phenylglyoxylic acid ethyl ester with acetylhydrazine, whereupon 1-phenylglyoxy acid ethyl ester-2-acetylhydrazone is formed, which, in a third stage, is converted, with hydrazine hydrate, in the presence of pyridine, into the abovementioned end product. This multi-stage synthesis can be represented by the following equations:

1st stage:

-continued

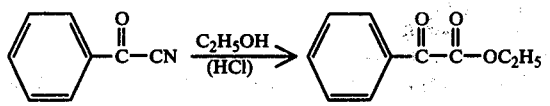

2nd stage:

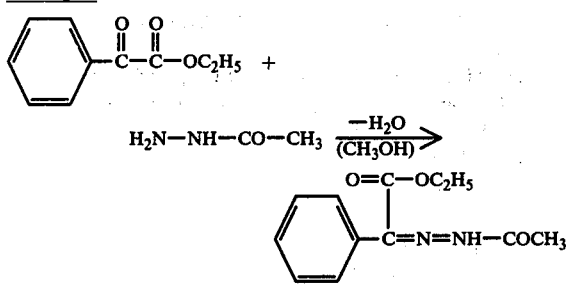

3rd stage:

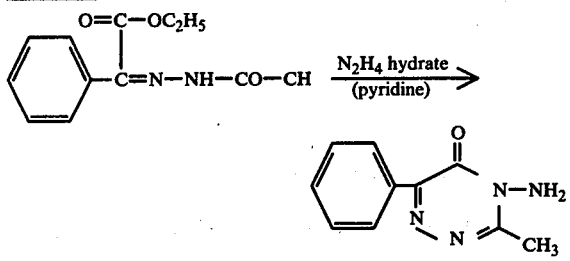

The process according to the invention is illustrated by the preparative Examples which follow:

EXAMPLE 1

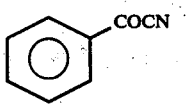 (1)

Process variant A 703 g (5 mol) of benzoyl chloride and 10 g of copper(I) cyanide were initially introduced into a 10-liter four-necked flask fitted with a stirrer, a thermometer, a reflux condenser and a dropping funnel and the mixture was heated to 190° C. 200 ml (5 mol) of anhydrous hydrocyanic acid were added dropwise in the course of 5 hours. In the course of the 5 hours, the internal temperature rose to 215° C. The hydrochloric acid formed was removed through the reflux condenser and the hydrocyanic acid was recycled into the reaction vessel by cooling. After the reaction had ended, the mixture was subjected to fractional distillation.

Yield: 624 g (95% of theory) of benzoyl cyanide with a melting point of 31° C.

Benzoic acid anhydride was formed as a by-product in an approximately 4–5% yield and could be separated off by distillation.

Process variant B 703 g (5 mol) of benzoyl chloride, 220.5 (4.28 mol) of sodium cyanide (95% pure) and 44.8 g (0.5 mol; approx. 16.9% by weight) of copper(I) cyanide were mixed in a 2-liter three-necked flask. A slight evolution of heat took place. The suspension was brought to an external temperature of 220°–240° C., whilst stirring, by means of an oil bath. In the course of 5 hours the internal temperature rose from 196° to 216° C. The black reaction mixture which was of low viscosity, was filtered cold and the salt residue was washed with 250 ml of ethyl acetate (o-dichlorobenzene could also have been used) and discarded. After distilling off the ethyl acetate, the filtrate was fractionated.

Yield: 604 g (92% of theory) of benzoyl cyanide with a melting point of 31° C.

Benzoic acid anhydride and unconverted benzoyl chloride were obtained as the by-product.

Process variant C (Complete conversion of benzoyl chloride)

703 g (5 mol) of benzoyl chloride were mixed with 245 g (4.75 mol) of sodium cyanide (95% pure) and 22.4 g (0.25 mol) of copper(I) cyanide (approx. 8.4% by weight).

The mixture was stirred for 4 hours at an external temperature of 220°–240° C. and during this time the internal temperature had risen from 196° to 216° C.

In order to convert the remaining 5% of benzoyl chloride, the mixture was stirred for a further 2 hours at an external temperature of 240° C.; the internal temperature rose from 216° to 218° C. The reaction mixture was filtered and the material on the filter was washed with about 250 ml of ethyl acetate or o-dichlorobenzene. The filtrate was fractionated. Yield: 537 g (82% of theory) of benzoyl cyanide with a melting point of 31° C.

Benzoic acid anhydride was obtained as the distillation residue.

Process variant D

One liter of o-dichlorobenzene was added to 241 g (4.8 mol) of sodium cyanide (98% pure) and 13.5 g (0.15 mol) of copper(I) cyanide in a 3 liter autoclave. The mixture was dehydrated by distilling off about 300 ml of o-dichlorobenzene. After adding 703 g (5 mol) of benzoyl chloride, the mixture was heated to 210° C. for 3 hours. A pressure of 2–3 bars developed. After cooling, the mixture was filtered. The filtrate was fractionated using a 30 cm silver jacketed column.

Yield: 757 g (88% of theory) of benzoyl cyanide.

The distillation residue contained benzoic acid anhydride.

EXAMPLE 2

78.5 g (1 mol) of acetyl chloride, 48.5 g (0.97 mol) of sodium cyanide, 2.7 g of copper(I) cyanide and 80 ml of o-dichlorobenzene were introduced into an autoclave and the mixture was warmed to 150° C. for 2 hours, whilst stirring. After cooling, the autoclave was opened and the mixture was filtered off from the salt residue. After fractional distillation, 48.5 g (70% of theory) of acetyl cyanide having a boiling point of 93° C. were obtained.

EXAMPLE 3

175 g (1 mol) of 3-chlorobenzoyl chloride, 48.5 g (0.97 mol) of sodium cyanide and 2.7 g of copper(I) cyanide were mixed in a three-necked flask and the mixture was warmed to 220° C. in the course of 90 minutes, whilst stirring. the reaction product was removed from the sodium chloride by applying a vacuum. Fractional distillation gave 155 g (94% of theory) of 3-chlorobenzoyl cyanide; boiling point: 112°–115° C. at 12 mm Hg.

EXAMPLE 4

175 g (1 mol) of 4-chlorobenzoyl chloride, 48.5 g (0.97 mol) of sodium cyanide and 2.7 g of copper(I) cyanide were mixed in a three-necked flask and treated as in Example 3. After fractional distillation 158 g (96% of theory) of 4-chlorobenzoyl cyanide were obtained; boiling point: 114°–116° C. at 13 mm Hg.

EXAMPLE 5

101 g (0.33 mol) of stearyl chloride were slowly warmed with 15 g (0.30 mol) of sodium cyanide and 2.7 g of copper(I) cyanide to 230° C. and the mixture was kept at this temperature for 1 hour. After cooling, the mixture was diluted with ethyl acetate, the sodium chloride was filtered off, the filtrate was concentrated and the reaction was distilled.

After a small amount of first runnings of stearyl chloride, 70 g (76% of theory) of stearyl cyanide with a boiling point of 228°–236° C. at 0.3 mm Hg were obtained.

EXAMPLE 6

203 g (1 mol) of isophthalic acid dichloride, 97 g (1.94 mol) of sodium cyanide and 5.4 g (0.06 mol) of copper(I) cyanide were mixed in a three-necked flask fitted with a stirrer, a reflux condenser and a thermometer and the mixture was heated to 230° C. for 1 hour. The reaction was exothermic. After cooling, 300 ml of ethyl acetate were added and the sodium chloride was filtered off. Fractional distillation gave 125 g (68% of theory) of isophthalic acid dicyanide; boiling point: 145°–150° C. at 0.2 mm Hg.

EXAMPLE 7

203 g (1 mol) of terephthalic acid dichloride, 97 g (1.94 mol) of sodium cyanide and 5.4 g of copper(I) cyanide were mixed in a reaction vessel, whilst stirring, and the mixture was slowly heated to 220° C. A distinctly exothermic reaction took place. After 90 minutes at 276° C., the mixture was allowed to cool and 400 ml of acetone were added. The residue was separated off by filtration and terephthalic acid dicyanide was obtained from the filtrate by fractional distillation.

Yield: 116 g (63% of theory) of terephthalic acid dicyanide. Boiling point: 82°–90° C. at 0.2 mm Hg.; melting point: 134°–136° C. (from wash benzine).

EXAMPLE 8

In the manner described above, 170 g (1 mol) of p-methoxybenzoyl chloride and 64.5 g (0.99 mol) of potassium cyanide and 1.17 g (0.1 mol) of zinc cyanide were mixed, whilst stirring, and the mixture was heated to 210° C. for 1 hour. A distillation bridge was then connected and the reaction product was separated from the residue direct. On subsequent fractionation, 138 g (86% of theory) of p-methoxybenzoyl cyanide with a melting point of 63° C. were obtained.

EXAMPLE 9

In the manner described above, 184 g (1 mol) of p-ethoxybenzoyl chloride, 62.5 g (0.96 mol) of potassium cyanide and 3.6 g (0.04 mol) of copper(I) cyanide were reacted with one another at 215° C. After working up, 159 g (91% of theory) of p-ethoxybenzoyl cyanide were obtained; melting point 43° C.

EXAMPLE 10

After adding 9 g (0.1 mol) of copper(I) cyanide, 175 g (1 mol) of m-chlorobenzoyl chloride were heated to 215° C. in a three-necked apparatus fitted with a stirrer, a reflux condenser and a dropping funnel and converted to m-chlorobenzoyl cyanide by the dropwise addition of 27 g (1 mol) of anhydrous hydrocyanic acid in the course of 3 hours.

After fractional distillation, 144 g (87% of theory) of m-chlorobenzoyl cyanide were obtained; boiling point: 112°–114° C. at 12 mm Hg.

It will be understood that the specification and examples are illustrative but not limitative of the present invention and that other embodiments within the spirit and scope of the invention will suggest themselves to those skilled in the art.

What is claimed is:

1. Process for the preparation of acyl cyanide

wherein
R is alkyl or substituted alkyl with 1 to 8 carbon atoms, wherein the substituents are selected from alkoxy or carbalkoxy of up to 4 carbon atoms in the alkoxy moiety, nitro, nitrile and halo; cyano-carbonyl substituted alkyl; cycloalkyl or substituted cycloalkyl with 3 to 12 carbon atoms wherein the substituent is selected from alkyl, alkoxy and carbalkoxy of up to 4 carbon atoms in each alkyl moiety, nitro, nitrile and halo; aryl or substituted aryl wherein the substitutents are selected from alkyl, alkoxy and carbalkoxy of up to 4 carbon atoms in the alkyl moiety, nitro and halo; or represents an optionally substituted 5-membered or 6-membered heterocyclic radical which can additionally also be fused with a benzene ring, wherein said substituents are selected from alkyl, alkoxy and carbalkoxy of up to 4 carbon atoms in each alkyl moiety, nitro, nitrile and halo;
which process comprises reacting an acid halide of the formula

wherein
R' is alkyl or substituted alkyl with 1 to 8 carbon atoms, wherein the substituents are selected from alkoxy or carbalkoxy of up to 4 carbon atoms in the alkoxy moiety, nitro, nitrile and halo; or

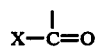

substituted alkyl; cycloalkyl or substituted cycloalkyl with 3 to 12 carbon atoms wherein the substituent is selected from alkyl, alkoxy and carbalkoxy of up to 4 carbon atoms in each alkyl moiety, nitro, nitrile and halo; aryl or substituted aryl wherein the substituents are selected from alkyl, alkoxy and carbalkoxy of up to 4 carbon atoms in the alkyl moiety, nitro and halo; or represents an optionally substituted 5-membered or 6-membered heterocyclic radical which can additionally also be fused with a benzene ring, and X is halogen, with an alkali metal cyanide or anhydrous hydrocyanic acid in the presence of a heavy metal cyanide, at a temperature of between 100° C. and 300° C.

2. Process as claimed in claim 1 wherein the reaction is carried out in the presence of a diluent.

3. Process as claimed in claim 1 wherein R is alkyl.

4. Process as claimed in claim 1 wherein R is substituted alkyl.

5. Process as claimed in claim 1 wherein R is alkyl substituted with a

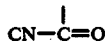

group.

6. Process as claimed in claim 1 wherein R is cycloalkyl or substituted cycloalkyl of from 5 to 6 ring carbon atoms.

7. Process as claimed in claim 1 wherein R is aryl or substituted aryl selected from phenyl and naphthyl and wherein the substituents are selected from alkyl of up to 4 carbon atoms, alkoxy or carbalkoxy of up to 4 carbon atoms in the alkyl moiety, nitrogen and halogen.

8. Process as claimed in claim 1 wherein R is a 5- or 6membered heterocyclic radical wherein the hetero atoms are selected from 1 to 3 oxygen, sulfur and nitrogen atoms.

9. Process as claimed in claim 1 wherein R' is alkyl substituted with an

group.

10. Process as claimed in claim 1 wherein R' is straight-chain or branched alkyl or substituted alkyl of from 1 to 4 carbon atoms, and the substitutents are selected from alkoxy of from 1 to 4 carbon atoms, carbalkoxy with from 1 to 4 carbon atoms, in the alkoxy group, nitro, nitrile and halogen; cycloalkyl or substituted cycloalkyl of from 5 or 6 carbon atoms in the ring system, and the substituents are selected from alkyl with 1 to 4 carbon atoms, alkoxy or carbalkoxy with, in either case, up to 4 carbon atoms in the alkyl part, nitro, nitrile and halogen; phenyl or naphthyl, substituted phenyl or naphthyl, where the substituents are selected from alkyl with 1 to 4 carbon atoms, alkoxy or carbalkoxy with, in each case, up to 4 carbon atoms in the alkyl part, nitro and halogen; or a 5-membered or 6-membered heterocyclic radical which can contain 1 to 3 hetero atoms selected from oxygen, sulfur and nitrogen in the ring and which may be substituted with substituents selected from alkyl, with 1 to 4 carbon atoms, alkoxy or carbalkoxy with, in either case, up to 4 carbon atoms in the alkyl part, nitro, nitrile and halogen, and which heterocyclic radical may be fused with a benzene ring.

11. Process as claimed in claim 1 wherein X is fluorine, chlorine or bromine.

12. Process as claimed in claim 1 wherein the reaction temperature is between 150° and 250° C.

13. Process as claimed in claim 1 wherein the acid halide of the formula II is employed in at least a stoichiometric amount, relative to the alkali metal cyanide.

14. Process as claimed in claim 1 wherein the cyanide reactant is an alkali metal cyanide selected from sodium or potassium cyanide.

15. Process as claimed in claim 1 wherein the said heavy metal cyanide is copper (I) cyanide, copper (II) cyanide or zinc (II) cyanide or a complex compound thereof with an alkali metal cyanide.

16. Process as claimed in claim 2 wherein said diluent is a dichlorobenzene.

17. Process as claimed in claim 1 wherein the acid halide of the formula II is an aromatic acid halide or an aromatic diacid dihalide.

18. Process as claimed in claim 17 wherein said acid halide (II) is a benzoyl halide.

19. Process as claimed in claim 18 wherein said benzoyl halide is benzoyl chloride.

20. Process as claimed in claim 1 wherein said acyl cyanide is benzoyl cyanide and the said acid halide is benzoyl halide.

21. Process as claimed in claim 1 wherein said acyl cyanide is 3-benzoyl cyanide and the said acid halide is 3-benzoyl halide.

22. Process as claimed in claim 1 wherein said acyl cyanide is terephthalic acid dicyanide and said halide is a terephthalic acid dihalide.

23. Process as claimed in claim 1 wherein said acyl cyanide is p-methoxybenzoyl cyanide and said halide is p-methoxybenzoyl halide.

24. Process as claimed in claim 1 wherein said acyl cyanide is p-ethoxybenzoyl cyanide and said halide is p-ethoxybenzoyl halide.

* * * * *